(12) United States Patent
Ozawa et al.

(10) Patent No.: US 9,622,961 B2
(45) Date of Patent: Apr. 18, 2017

(54) WATER-SOLUBLE POLYALKYLENE OXIDE-MODIFIED PRODUCT

(75) Inventors: Hitoshi Ozawa, Osaka (JP); Yusuke Nishikawa, Himeji (JP); Tatsuo Ohtani, Himeji (JP); Tsuyoshi Masuda, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 288 days.

(21) Appl. No.: 13/979,492

(22) PCT Filed: Dec. 26, 2011

(86) PCT No.: PCT/JP2011/080085
§ 371 (c)(1),
(2), (4) Date: Jul. 12, 2013

(87) PCT Pub. No.: WO2012/096124
PCT Pub. Date: Jul. 19, 2012

(65) Prior Publication Data
US 2013/0310465 A1 Nov. 21, 2013

(30) Foreign Application Priority Data
Jan. 13, 2011 (JP) ................................. 2011-004776

(51) Int. Cl.
*A61K 8/87* (2006.01)
*A61Q 5/02* (2006.01)
(Continued)

(52) U.S. Cl.
CPC ................. *A61K 8/87* (2013.01); *A61Q 5/02* (2013.01); *A61Q 19/00* (2013.01); *C08G 18/282* (2013.01);
(Continued)

(58) Field of Classification Search
None
See application file for complete search history.

(56) References Cited

U.S. PATENT DOCUMENTS

| 4,079,028 | A | | 3/1978 | Emmons et al. | |
|---|---|---|---|---|---|
| 5,500,475 | A | * | 3/1996 | Eicken et al. | ................ 524/591 |

(Continued)

FOREIGN PATENT DOCUMENTS

| JP | 7-501094 A | 2/1995 |
|---|---|---|
| JP | 2004-525995 A | 8/2004 |

(Continued)

OTHER PUBLICATIONS

Notification of Transmittal of Translation of the International Preliminary Report on Patentability (Forms PCT/IB/326) of International Application No. PCT/JP2011/080085 mailed Jul. 25, 2013 with Forms PCT/IB/373, PCT/IB/338 and PCT/ISA/237.
International Search Report for PCT/JP2011/080085, Maling Date of Jan. 31, 2012.
Howard, Paul R., et al., "Formulating with Combinations of HEUR Associative Thickeners", J. Coating Technology, Jan. 1992, vol. 64, No. 804, pp. 87-94.

(Continued)

*Primary Examiner* — Jeffrey Washville
(74) *Attorney, Agent, or Firm* — Westerman, Hattori, Daniels & Adrian, LLP

(57) ABSTRACT

The present invention provides a water-soluble polyalkylene oxide-modified product which is nonionic, has a high thickening effect and is also excellent in transparency, and an emulsion composition and a cosmetic material containing the same. More specifically, the present invention provides a water-soluble polyalkylene oxide-modified product obtained by reacting a monovalent hydrophobic alcohol, a linear diol compound, a polyalkylene oxide compound and a diisocyanate compound, and an emulsion composition and a cosmetic material containing the same.

7 Claims, 2 Drawing Sheets

(51) Int. Cl.
    *A61Q 19/00* (2006.01)
    *C08G 18/48* (2006.01)
    *C08G 18/66* (2006.01)
    *C08G 18/73* (2006.01)
    *C08G 18/75* (2006.01)
    *C08G 18/28* (2006.01)
    *C08G 18/32* (2006.01)

(52) U.S. Cl.
    CPC ..... *C08G 18/3206* (2013.01); *C08G 18/4833* (2013.01); *C08G 18/4845* (2013.01); *C08G 18/6674* (2013.01); *C08G 18/73* (2013.01); *C08G 18/755* (2013.01); *C08G 18/758* (2013.01); *A61K 2800/10* (2013.01); *A61K 2800/262* (2013.01)

(56) References Cited

U.S. PATENT DOCUMENTS

2004/0028742 A1    2/2004  Bigorra Llosas et al.
2008/0108775 A1*   5/2008  Schieferstein et al. ......... 528/66
2012/0094880 A1    4/2012  Ozawa et al.

FOREIGN PATENT DOCUMENTS

WO    2010/150875 A1    12/2010
WO    2012/024610 A1     2/2012

OTHER PUBLICATIONS

Extended European Search Report dated Nov. 17, 2016, issued in corresponding European Patent Application No. EP11855559.8 (6 pages).

* cited by examiner

Viscosity curve of 3% by mass aqueous solution

WATER-SOLUBLE POLYALKYLENE OXIDE-MODIFIED PRODUCT

TECHNICAL FIELD

The present invention relates to a water-soluble polyalkylene oxide-modified product. More specifically, the present invention relates to a water-soluble polyalkylene oxide-modified product having a high thickening effect and excellent transparency.

BACKGROUND ART

In recent years, as a thickening agent for paints, cosmetics and the like, instead of the conventional polyacrylic acid-based thickening agent, a polyurethane-based thickening agent which is nonionic and is of a type that allows the viscosity to be increased by aggregation of hydrophobic groups has attracted attention.

Such polyurethane-based thickening agents are capable of allowing the viscosity to be increased by association of hydrophobic groups which the agents have at each terminal thereof. In addition, the agents are excellent in salt tolerance since they are nonionic, and have the advantage of being capable of imparting new rheological properties.

As the technique, it is known that the longer the chain length of a hydrophobic group present at the terminal is, the more enhanced the thickening effect is (Non-Patent Document 1).

As the polyurethane-based thickening agent, a material having three hydrophobic groups bound through a hydrophilic polyester group with a molecular weight of at least 1,500, wherein at least two groups of the hydrophobic groups are located at the terminal groups (Patent Document 1), and a material obtained by the reaction of:

(a) at least one water-soluble polyether polyol,
(b) at least one water-insoluble organic polyisocyanate,
(c) at least one monofunctional hydrophobic organic compound selected from a compound containing a hydrogen atom reactive with an isocyanate and an organic monoisocyanate, and
(d) at least one polyhydric alcohol or polyhydric ether alcohol (Patent Document 2, Patent Document 3) are known.

Moreover, a polyurethane-based thickening agent characterized by containing a monohydric alcohol with at least one other polar group or a trihydric alcohol as a polyhydric alcohol is also known (Patent Document 4).

PRIOR ART DOCUMENTS

Non-Patent Documents

Non-Patent Document 1: J. Coating Technology, Vol. 64, No. 804, pp. 87-94 (1992)

Patent Documents

Patent Document 1: Japanese Patent Laid-Open No. 54-80349
Patent Document 2: U.S. Pat. No. 4,155,892
Patent Document 3: U.S. Pat. No. 4,079,028
Patent Document 4: National Publication of International Patent Application No. 1995-501094

SUMMARY OF THE INVENTION

Problems to be Solved by the Invention

With regard to the polyurethane-based thickening agents obtained by the conventional technique, as described in the above-mentioned Non-Patent Document 1, the thickening effect becomes large as the number of carbon atoms of the alcohol present at the terminal increases. However, as the number of carbon atoms of the terminal alcohol increases, the affinity for water becomes poor, the aqueous solution on thickening tends to cause a decrease in transparency, and the feeling of stickiness tends to be given. Therefore, for example, there are problems that, when the polyurethane-based thickening agent is added as a cosmetic ingredient, the impression from use becomes heavy, and the like.

Means for Solving the Problems

As a result of intensive studies for solving the above problems, the present inventors have found that a water-soluble polyalkylene oxide-modified product obtained by reacting a polyalkylene oxide compound, a specific linear diol compound, a monovalent hydrophobic alcohol and a diisocyanate compound, provides an aqueous solution exhibiting high viscosity with a small amount thereof and excellent in transparency, and thus the present invention has been completed.

That is, the present invention relates to a water-soluble polyalkylene oxide-modified product described below, and an emulsion composition and a cosmetic material containing the same.

Item 1. A water-soluble polyalkylene oxide-modified product obtained by reacting a monovalent hydrophobic alcohol of the general formula (I):

[Chem. 1]

$$R^1\text{—OH} \qquad \qquad \text{(I)}$$

wherein $R^1$ represents an alkyl group with 6 to 14 carbon atoms, a linear diol compound of the general formula (II):

[Chem. 2]

$$HO\text{—}R^2\text{—}OH \qquad \qquad \text{(II)}$$

wherein $R^2$ represents a linear alkylene group with 5 to 10 carbon atoms, a polyalkylene oxide compound of the general formula (III):

[Chem. 3]

$$HO\text{—}(CH_2CHR^3\text{—}O)_n\text{—}H \qquad \qquad \text{(III)}$$

wherein $R^3$ represents hydrogen atom or a methyl group and n represents an integer of 90 to 900, and a diisocyanate compound of the general formula (IV):

[Chem. 4]

$$O=C=N\text{—}R^4\text{—}N=C=O \qquad \qquad \text{(IV)}$$

wherein $R^4$ represents a methyl diphenylene group, a hexamethylene group, a methyl dicyclohexylene group, a 3-methyl-3,5,5-trimethyl cyclohexylene group, a dimethyl phenylene group or a tolylene group.

Item 2. The water-soluble polyalkylene oxide-modified product according to item 1, wherein the polyalkylene oxide compound is a polyalkylene oxide compound selected from the group consisting of polyethylene oxide with a number average molecular weight of 4,000 to 30,000 and a polyethylene oxide/polypropylene oxide copolymer with a number average molecular weight of 4,000 to 30,000.

Item 3. The water-soluble polyalkylene oxide-modified product according to item 1 or 2, wherein the amount of the linear diol compound used is 0.5 to 2.5 moles relative to 1 mole of the polyalkylene oxide compound.

Item 4. The water-soluble polyalkylene oxide-modified product according to any one of items 1 to 3, wherein the amount of the hydrophobic alcohol used is 0.5 to 2.5 moles relative to 1 mole of the polyalkylene oxide compound.

Item 5. The water-soluble polyalkylene oxide-modified product according to any one of items 1 to 4, wherein the diisocyanate compound is at least one selected from the group consisting of dicyclohexylmethane-4,4'-diisocyanate, 1,6-hexamethylene diisocyanate and 3-isocyanatomethyl-3,5,5-trimethylcyclohexyl=isocyanate.

Item 6. An emulsion composition, comprising the water-soluble polyalkylene oxide-modified product according to any one of items 1 to 5 in an amount of 0.01 to 10% by mass.

Item 7. A cosmetic material, comprising the water-soluble polyalkylene oxide-modified product according to any one of items 1 to 5 in an amount of 0.01 to 10% by mass.

Moreover, the water-soluble polyalkylene oxide-modified product according to the present invention is preferably characterized in that the concentration of the urethane group in the water-soluble polyalkylene oxide-modified product is in the range of 1.0 to 3.0%, and the transmittance of a 3% by mass aqueous solution thereof at a wavelength of 425 nm with a quartz cell having a length of 1 cm is 30% or more.

The water-soluble polyalkylene oxide-modified product according to the present invention obtained by reacting the compounds of the general formulae (I) to (IV) is represented by the following general formula (V):

[Chem. 5]

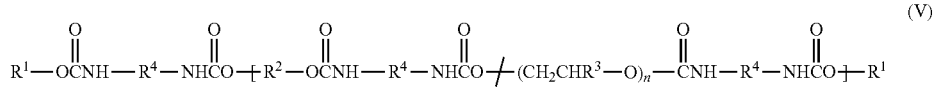

(V)

wherein $R^1$ to $R^4$ and n are as defined above for the general formulae (I) to (IV), and "/" refers to allowing two kinds of repeating structural units in square brackets put in the preceding and following strings to form ester linkages in any order.

For example, the water-soluble polyalkylene oxide-modified product of the general formula (V) is a material of the following formula:

of preventing the paint from dribbling and smoothness by the addition of a small amount thereof.

The present invention provides a water-soluble polyalkylene oxide-modified product obtained by reacting a monovalent hydrophobic alcohol, a linear diol compound, a polyalkylene oxide compound and a diisocyanate compound. Furthermore, the present invention also provides a cosmetic material and an emulsion composition for paint, in which the water-soluble polyalkylene oxide-modified product according to the present invention is used as a thickening agent.

Effects of the Invention

Since the water-soluble polyalkylene oxide-modified product according to the present invention has a high thickening effect by the addition of a small amount thereof and an aqueous solution thereof is excellent in transparency, it is possible by utilizing this to provide a cosmetic material which gives little feeling of stickiness, a paint which is excellent in preventing the paint from dribbling and smoothness of the coating, and the like.

[Chem. 6]

Figure 1:
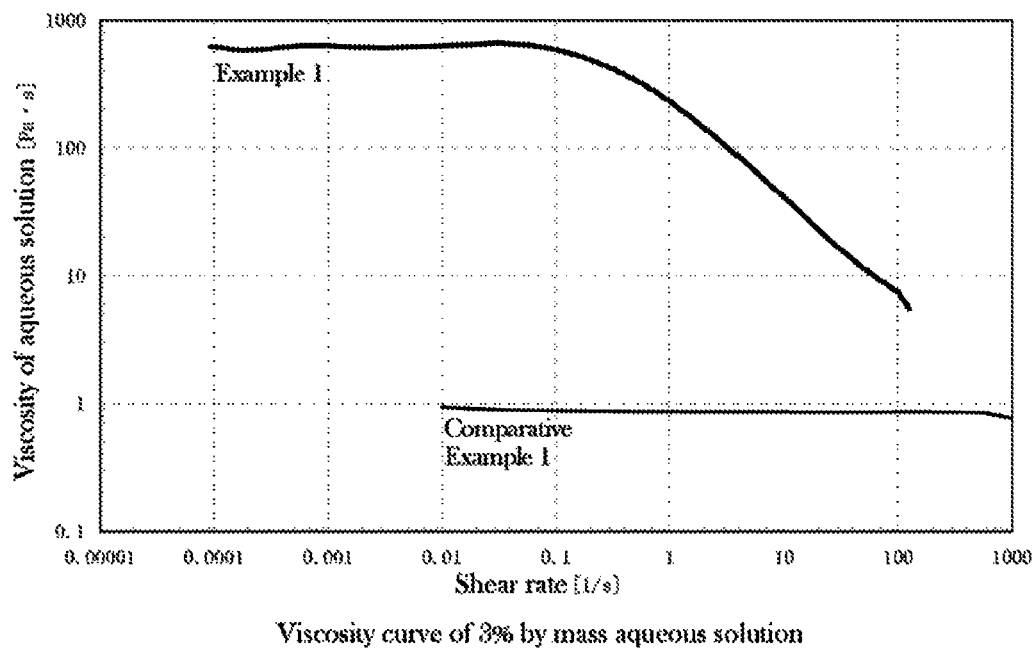
FIG. 1 shows a relationship between the shear rate and the viscosity of the aqueous solution for the water-soluble polyalkylene oxide-modified product obtained (3% by mass aqueous solution).

wherein $R^1$ to $R^4$ and n are as defined above for the general formulae (I) to (IV).

Since an aqueous solution of the water-soluble polyalkylene oxide-modified product according to the present invention is excellent in transparency, it is possible to maintain its transparency when the aqueous solution is used for a cosmetic material, and since it is possible to attain a thickening effect by the addition of a small amount thereof, the feeling of stickiness can be reduced. Moreover, the water-soluble polyalkylene oxide-modified product according to the present invention has a high thickening effect also on a paint which has been increasingly shifting to the water-based paint in recent years from the viewpoints of environmental problems and safety, and can impart the paint with an effect

MODE FOR CARRYING OUT THE INVENTION

The water-soluble polyalkylene oxide-modified product according to the present invention is obtained by reacting a monovalent hydrophobic alcohol, a linear diol compound, a polyalkylene oxide compound and a diisocyanate compound.

The monovalent hydrophobic alcohol is represented by the general formula (I):

[Chem. 7]

$R^1$—OH <span>(I).</span>

$R^1$ is a hydrocarbon group of the hydrophobic alcohol, and specifically includes an alkyl group, such as a linear alkyl group and a branched alkyl group, with 6 to 14 carbon atoms.

Examples of the linear alkyl group include a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosyl group, a n-heneicosyl group, and a n-docosyl group.

Examples of the branched alkyl group include a 2-ethylhexyl group, an isodecyl group, an isotridecyl group, and an isostearyl group.

As the monovalent hydrophobic alcohol, preferred is such a monovalent hydrophobic alcohol with the solubility in water in the range of 0.4% by mass or less, and examples thereof include hexyl alcohol, heptyl alcohol, octyl alcohol, nonyl alcohol, decyl alcohol, undecyl alcohol, dodecyl alcohol, tridecyl alcohol and tetradecyl alcohol, and more preferred are hexyl alcohol, octyl alcohol and decyl alcohol.

These monovalent hydrophobic alcohols may be used alone or in combination of two or more thereof.

The amount of the monovalent hydrophobic alcohol used is preferably 0.5 to 2.5 moles, more preferably 0.8 to 2.2, relative to 1 mole of the polyalkylene oxide compound. In case where the amount of the monovalent hydrophobic alcohol used is less than 0.5 moles, there is a possibility that the viscosity of an aqueous solution of the water-soluble polyalkylene oxide-modified product obtained is lowered. In case where the amount of the monovalent hydrophobic alcohol used exceeds 2.5 moles, there is a possibility that the transparency of an aqueous solution of the water-soluble polyalkylene oxide-modified product obtained is lowered.

The linear diol compound is represented by the general formula (II):

[Chem. 8]

$$HO-R^2-OH \qquad (II).$$

$R^2$ is a hydrocarbon group of the linear diol compound, and specifically includes a linear alkylene group with 5 to 10 carbon atoms.

Examples of the linear alkylene group include n-pentamethylene, n-hexamethylene, n-heptamethylene, n-octamethylene, n-nonamethylene, and n-decamethylene.

As the linear diol compound, preferred are 1,5-pentanediol, 1,6-hexanediol, 1,7-heptanediol, 1,8-octanediol and 1,9-nonanediol, and more preferred are 1,6-hexanediol and 1,9-nonanediol.

In addition, in case where a linear diol compound with the number of carbon atoms of less than 5 is used, the solubility in water of the water-soluble polyalkylene oxide-modified product obtained becomes extremely low and is gelled, and it cannot be used as a thickening agent.

Moreover, in case where a branched alkyldiol or a trihydric alcohol is used as the linear diol compound instead of a linear diol, the solubility in water of the water-soluble polyalkylene oxide-modified product obtained becomes extremely low and is gelled, and it cannot be used as a thickening agent.

These linear diol compounds may be used alone or in combination of two or more thereof.

The amount of the linear diol compound used is preferably 0.5 to 2.5 moles, more preferably 0.8 to 2.2 moles, relative to 1 mole of the polyalkylene oxide compound. In case where the amount of the linear diol compound used is less than 0.5 moles, there is a possibility that the transparency of the water-soluble polyalkylene oxide-modified product obtained is lowered. In case where the amount of the linear diol compound used exceeds 2.5 moles, the solubility in water of the water-soluble polyalkylene oxide-modified product obtained becomes extremely low, and there is a possibility of its gelling.

The polyalkylene oxide compound is represented by the general formula (III):

[Chem. 9]

$$HO-(CH_2CHR^3-O)_n-H \qquad (III).$$

$R^3$ is hydrogen atom or a methyl group and n represents an integer of 90 to 900.

Specific examples of the polyalkylene oxide compound include polyethylene oxide, polypropylene oxide, and polyethylene oxide/polypropylene oxide (preferably, a copolymer of ethylene oxide and propylene oxide). Among these polyalkylene oxide compounds, preferred is a polyalkylene oxide compound containing ethylene oxide groups in an amount of 70% by mass or more, and more preferred is a polyalkylene oxide compound containing ethylene oxide groups in an amount of 95% by mass or more. In case where the content of the ethylene oxide group is less than 70% by mass, there is a possibility that the viscosity of an aqueous solution of the water-soluble polyalkylene oxide-modified product obtained is lowered.

Moreover, the number average molecular weight of the polyalkylene oxide compound is preferably 4,000 to 30,000, more preferably 6,000 to 20,000. In case where the number average molecular weight of the polyalkylene oxide compound is less than 4,000, there is a possibility that the viscosity of an aqueous solution of the water-soluble polyalkylene oxide-modified product obtained is lowered. In case where the number average molecular weight of the polyalkylene oxide compound exceeds 30,000, there is a possibility that the solubility in water of the water-soluble polyalkylene oxide-modified product obtained is lowered.

The diisocyanate compound is represented by the general formula (IV):

[Chem. 10]

$$O=C=N-R^4-N=C=O \qquad (IV).$$

$R^4$ represents a methyl diphenylene group, a hexamethylene group, a methyl dicyclohexylene group, a 3-methyl-3,5,5-trimethyl cyclohexylene group, a dimethyl phenylene group or a tolylene group.

Specific examples of the diisocyanate compound include 4,4'-diphenylmethane diisocyanate (MDI), 1,6-hexamethylene diisocyanate (HDI), dicyclohexylmethane-4,4'-diisocyanate (HMDI), 3-isocyanatomethyl-3,5,5-trimethylcyclohexyl=isocyanate (IPDI), 1,8-dimethylbenzole-2,4-diisocyanate, and 2,4-tolylene diisocyanate (TDI). Among these diisocyanate compounds, from the viewpoint that the water-soluble polyalkylene oxide-modified product obtained is excellent in weather resistance and transparency, preferred are dicyclohexylmethane-4,4'-diisocyanate (HMDI), 1,6-hexamethylene diisocyanate (HDI) and 3-isocyanatomethyl-3,5,5-trimethylcyclohexyl=isocyanate (IPDI). These diisocyanate compounds may be used alone or in combination of two or more thereof.

The proportion of the polyalkylene oxide compound, the diol compound, the monovalent hydrophobic alcohol compound and the diisocyanate compound to be used is determined so that the concentration of urethane group in the water-soluble polyalkylene oxide-modified product calculated by the following equation is preferably 1.0 to 3.0%, more preferably 1.5 to 2.8%.

In case where the concentration of urethane group is less than 1.0%, there is a possibility that the transparency of an aqueous solution of the water-soluble polyalkylene oxide-modified product obtained deteriorates. In case where the concentration of urethane group exceeds 3.0%, the solubility in water of the water-soluble polyalkylene oxide-modified product obtained becomes low, and there is a possibility of its gelling.

[Math. 1]

$$\text{Concentration of urethane group } U\ (\%) =$$
$$\{(2 \times 43 \times [NCO])/\text{molecular weight}^*\} \times 100$$

*Molecular weight: {[polyalkylene oxide] ×
  (molecular weight of polyalkylene oxide compound)} +
  {[diol] × (molecular weight of linear diol compound) +
  {[hydrophobic alchohol] ×
  (molecular weight of hydrophobic alchohol)} +
  {[NCO] × (molecular weight of diisocyanate compound)}

[NCO]: number of moles of diisocyanate compound
[polyalkylene oxide]: number of moles of polyalkylene oxide compound
[diol]: number of moles of linear diol compound
[hydrophobic alcohol]: number of moles of monovalent hydrophobic alcohol Examples of the method for reacting the monovalent hydrophobic alcohol, the linear diol compound, the polyalkylene oxide compound and the diisocyanate compound include a method for reacting the compounds by dissolving or dispersing them in a reaction solvent such as toluene, xylene and dimethylformamide; and a method for reacting the compounds by milling (pulverizing) or melting their solids into powders or liquids to uniformly mix both materials and then by heating the mixture to a predetermined temperature. From the viewpoint of industrial practice, a method for reacting the compounds by continuously supplying each of raw materials in a heated and melted state, and mixing the materials in a multi-screw extruder, is preferred. The temperature of the reaction is in the range of 70 to 210° C., preferably in the range of 90 to 180° C., and more preferably 100 to 160° C. In case where the temperature of the reaction is less than 70° C., there is a possibility that the reaction becomes heterogeneous. In case where the temperature of the reaction exceeds 210° C., there is a possibility that the water-soluble polyalkylene oxide-modified product obtained decomposes and discolors. The reaction time may be appropriately set, so that the reaction is completed in accordance with the reaction temperature, the kind of the polyalkylene oxide compound, the linear diol compound, the monovalent hydrophobic alcohol and the diisocyanate compound to be used, and the like. In this context, the reaction time is defined as the average residence time determined by the following method using a multi-screw extruder. By supplying slight amounts of coloring agents (for example, pulverized red chalk and Blue No. 5) simultaneously with the polyalkylene oxide compound, the hydrophobic alcohol and the diisocyanate compound to the multi-screw extruder, and observing the color change of the discharged product, the average residence time may be measured as the time period to the point at which a portion of the product with the darkest color is discharged. The average residence time is adjusted to a time period in the range of 0.5 to 5.0 minutes, preferably 1.0 to 3.5 minutes and more preferably 1.5 to 3.0 minutes, by the amount supplied, the number of revolutions and the shape of the screw.

Moreover, when the water-soluble polyalkylene oxide-modified product is produced, from the viewpoint of promoting the reaction, a reaction accelerator such as triethylamine, triethanolamine, dibutyltin diacetate, dibutyltin dilaurate, stannous octoate and triethylenediamine may also be added in small amounts to the reaction system. The amount of the reaction accelerator used is preferably 200 to 2,000 ppm by mass, more preferably 500 to 1,000 ppm by mass, relative to the polyalkylene oxide compound.

Thus, the water-soluble polyalkylene oxide-modified product can be obtained by mixing the monovalent hydrophobic alcohol, the linear diol compound, the polyalkylene oxide compound and the diisocyanate compound in a suitable reactor such as an extruder to react them.

The water-soluble polyalkylene oxide-modified product thus obtained is represented by the following general formula (V):

[Chem. 11]

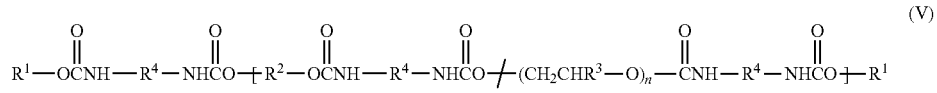

(V)

wherein $R^1$ to $R^4$ and n are as defined above for the general formulae (I) to (IV), and "/" refers to allowing two kinds of repeating structural units in square brackets put in the preceding and following strings to form ester linkages in any order.

For example, the water-soluble polyalkylene oxide-modified product represented by the general formula (V) is a material represented by the following formula:

[Chem. 12]

wherein $R^1$ to $R^4$ and n are as defined above for the general formulae (I) to (IV).

The water-soluble polyalkylene oxide-modified product obtained may be added to a cosmetic material or an emulsion composition, and also be dissolved therein during the production process thereof. Moreover, the modified product may be previously diluted with water; an aqueous solution containing a salt such as sodium chloride or a surfactant; an aqueous solution of diethylene glycol monobutyl ether, triethylene glycol monobutyl ether, polypropylene glycol, propylene glycol or the like; polyethylene glycol 200, or the like so as to allow the concentration thereof to be 5 to 50% by mass before use. From the viewpoint of maintaining the transparency of the aqueous solution obtained for a long period of time, it is preferred to dilute the modified product with water or polyethylene glycol 200 before use.

The transparency may be evaluated on the basis of the light transmittance at 425 nm obtained in case where a 3% by mass aqueous solution of the water-soluble polyalkylene oxide-modified product is charged into quartz glass having a length of 1 cm using a UV-visible spectrophotometer. The transmittance is preferably 30% or more, more preferably 40% or more and further preferably 50% or more. When the transmittance is less than 30%, there is a possibility that the transparency deteriorates in case where the water-soluble polyalkylene oxide-modified product is used as a cosmetic material.

Moreover, the viscosity of a 3% by mass aqueous solution of the water-soluble polyalkylene oxide-modified product according to the present invention is determined by measuring the viscosity at a shear rate in the range of 0.0001 to 1,000 [1/s] and at a temperature of 25° C. with a cone-and-plate rheometer (AR2000 manufactured by TA Instruments Inc.) using a cone (60 mm, cone angle 1°). In addition, its viscous behavior can be grasped in more detail by using a cone-and-plate rheometer, compared to the conventional method for measurement using a B-type viscometer.

Furthermore, the TI value A (ratio of the viscosity at a shear rate of 0.01 [1/S]/the viscosity at a shear rate of 0.1 [1/S]) of a 3% by mass aqueous solution of the water-soluble polyalkylene oxide-modified product according to the present invention is preferably in the range of 1.0 to 1.8, more preferably 1.0 to 1.5. The viscosity at a shear rate of 0.1 to 1.0 [1/s] is involved in the leveling properties developed when the water-soluble polyalkylene oxide-modified product according to the present invention is added to a paint, a cosmetic or the like, and in case where the TI value A is less than 1.0, it is not preferred because the storage stability deteriorates. In case where the TI value A exceeds 1.8, it is not preferred because dribbling is apt to occur on application.

Moreover, the TI value B (ratio of the viscosity at a shear rate of 10 [1/S]/the viscosity at a shear rate of 100 [1/S]) of a 3% by mass aqueous solution of the water-soluble polyalkylene oxide-modified product according to the present invention is preferably in the range of 3.0 to 9.0, more preferably 4.0 to 8.0. The viscosity at a shear rate of 10 to 100 [1/s] is involved in mixing and stirring developed when the water-soluble polyalkylene oxide-modified product according to the present invention is added to a paint, a cosmetic or the like, and in case where the TI value B is less than 3.0, it is not preferred because mixing and stirring deteriorates due to a small degree of decrease in viscosity on shearing. In case where the TI value B exceeds 9.0, it is not preferred because the ease of mixing with other ingredients deteriorates due to too large a degree of decrease in viscosity and dribbling is apt to occur on application.

In the present invention, the TI values A and B can be controlled by the total number of carbon atoms of the linear diol compound and carbon atoms of the monovalent hydrophobic alcohol in the water-soluble polyalkylene oxide-modified product, and it is preferred that the total of the number of carbon atoms of the linear diol compound and the number of carbon atoms of the monovalent hydrophobic alcohol may be in the range of 12 to 19. In case where the total of the number of carbon atoms of the linear diol compound and the number of carbon atoms of the monovalent hydrophobic alcohol is less than 12, it is not preferred because the TI values A and B become less than 1.1. In case where the total of the number of carbon atoms of the linear diol compound and the number of carbon atoms of the monovalent hydrophobic alcohol exceeds 19, it is not preferred because the TI value B exceeds 9.0 although the TI value A is in the range of 1.0 to 1.8.

Furthermore, a cosmetic material and an emulsion composition for paint, both of which contain the water-soluble polyalkylene oxide-modified product according to the present invention, are provided. The cosmetic material and the emulsion composition may be prepared in a usual manner. Depending on the physical properties such as the viscosity and transparency, and the concentration, the physical properties or the like of other formulation ingredients, the water-soluble polyalkylene oxide-modified product can be appropriately added to these cosmetic material and emulsion composition, preferably in an amount of 0.01 to 10% by mass, more preferably in an amount of 0.1 to 5.0% by mass.

EXAMPLES

The present invention will be described below in more detail with reference to examples and comparative examples, but the present invention is not limited to these examples.

After a water-soluble polyalkylene oxide-modified product in the form of pellets obtained from each example was immersed in liquid nitrogen, it was milled so as to allow the median particle diameter to be 100 μm and was subjected to the following evaluations.

Evaluation Methods (1) Viscosity of Aqueous Solution

To 297 g of ion-exchanged water or a 3% by mass aqueous sodium chloride solution, 9.0 g of a water-soluble polyalkylene oxide-modified product was added and stirred for 3 hours under the condition of 30° C. and 300 rpm to obtain a 3% by mass aqueous solution of the water-soluble polyalkylene oxide-modified product.

The resulting aqueous solution was measured for the viscosity of the aqueous solution at a shear rate in the range of 0.0001 to 1,000 [1/s] and at 25° C. with a cone-and-plate rheometer (AR2000 manufactured by TA Instruments Inc.) using a cone (60 mm, cone angle 1°).

Moreover, with regard to the water-soluble polyalkylene oxide-modified products obtained in Example 1 and Comparative Example 1, the relationship between the shear rate and the viscosity of the aqueous solution is shown in FIG. 1.

(2) TI Value

From the measurement results of the above-mentioned (1) Viscosity of aqueous solution, the TI value A and TI value B were calculated according to the following equations.

$$TI\ value\ A = (\text{viscosity at a shear rate of } 0.01[1/s])/(\text{viscosity at a shear rate of } 0.1[1/S])$$

$$TI\ value\ B = (\text{viscosity at a shear rate of } 10[1/s])/(\text{viscosity at a shear rate of } 100[1/S])$$

(3) Transparency

Into each quartz glass with a thickness of 1 cm, 4.5 ml of each of an aqueous solution and a 3% by mass aqueous sodium chloride solution, both of which contain a water-soluble polyalkylene oxide-modified product obtained in the same manner as in the above-mentioned (1) in an amount of 3% by mass, and 4.5 ml of shampoo obtained in each of Examples 11 to 15 and Comparative Examples 10 to 12 described below were separately charged, after which each liquid was centrifuged (1,800 rpm) to remove air bubbles and was measured for the light transmittance at 425 nm with a UV-visible spectrophotometer (UV-3150: Shimadzu Corp.) to evaluate the transparency.

(4) Viscosity of Cold Cream and Shampoo

Cold creams obtained in Examples 6 to 10 and Comparative Examples 7 to 9 and shampoos obtained in Examples 11 to 15 and Comparative Examples 10 to 12 described below were each measured for the viscosity at a shear rate of 1 [1/s] and at 25° C. with a cone-and-plate rheometer (AR2000 manufactured by TA Instruments Inc.) using a cone (60 mm, cone angle 1°).

(5) Stickiness

To a sheet of artificial leather (Sapurare manufactured by Idemitsu Petrochemical Co., Ltd.), 0.2 ml of cold cream obtained in Examples 1 to 4 and Comparative Examples 7 to 9 described below was applied and the sheet was tautly stretched, after which the average frictional coefficient μ and the fluctuation range of the average frictional coefficient (MMD) were measured under the following test conditions using Toray Friction Tester (manufactured by Kato Tech Co., Ltd., model: KES-SE).

Sensor: silicone
Load: 50 [g]
Velocity: 5 [mm/second]

(i) Average Frictional Coefficient (MIU)

The average frictional coefficient is correlated with the slipperiness and non-slipperiness capable of feeling when rubbing the surface of an object. The larger the value is, the less slippery the object is.

Figure 2:
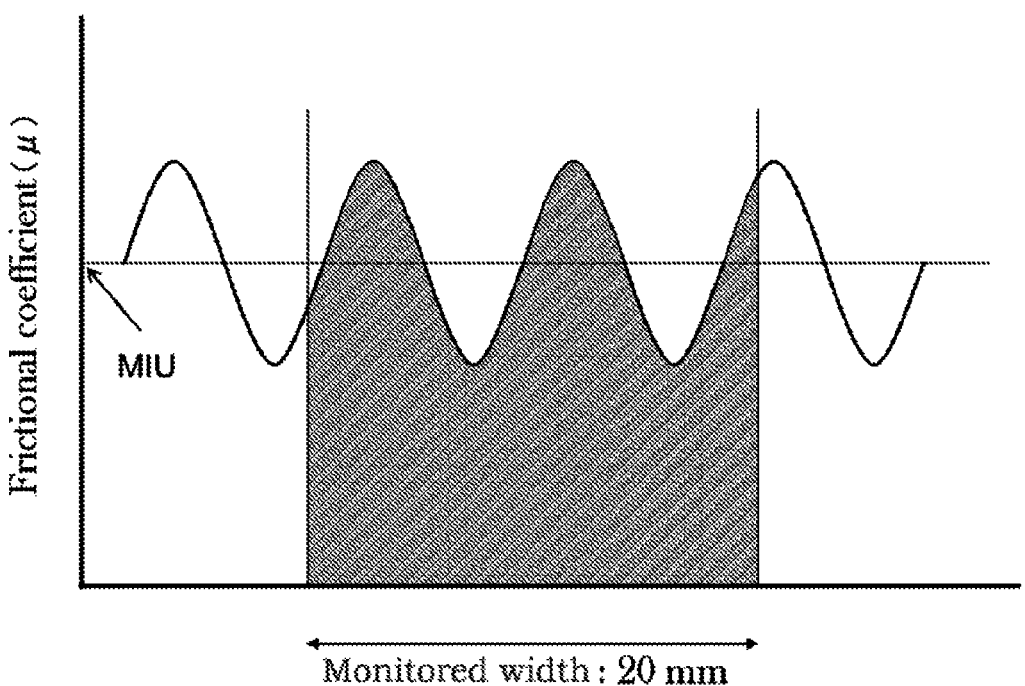
FIG. 2 shows a schematic illustration for determining the average frictional coefficient (MIU) from a result of monitoring the frictional coefficient μ.

A schematic illustration for determining the average frictional coefficient (MIU) from a result of monitoring the frictional coefficient μ is shown in FIG. 2.

As shown in FIG. 2, a scan over the artificial leather to which a cold cream has been applied is performed to monitor the frictional coefficient μ. Next, in the monitored width of 20 mm, the integral of the frictional coefficient μ is calculated (the shaded portion in FIG. 2). The average frictional coefficient (MIU) is determined by dividing the integrated value by the monitored width (20 mm).

In case where the value of MIU is not more than 0.4, it can be observed that the slipperiness is good and there is little stickiness.

(ii) Fluctuation Range of Average Frictional Coefficient (MMD)

The fluctuation range of the average frictional coefficient is correlated with the smoothness and roughness capable of feeling when rubbing the surface of an object. The larger the value is, the rougher the surface is.

Figure 3:
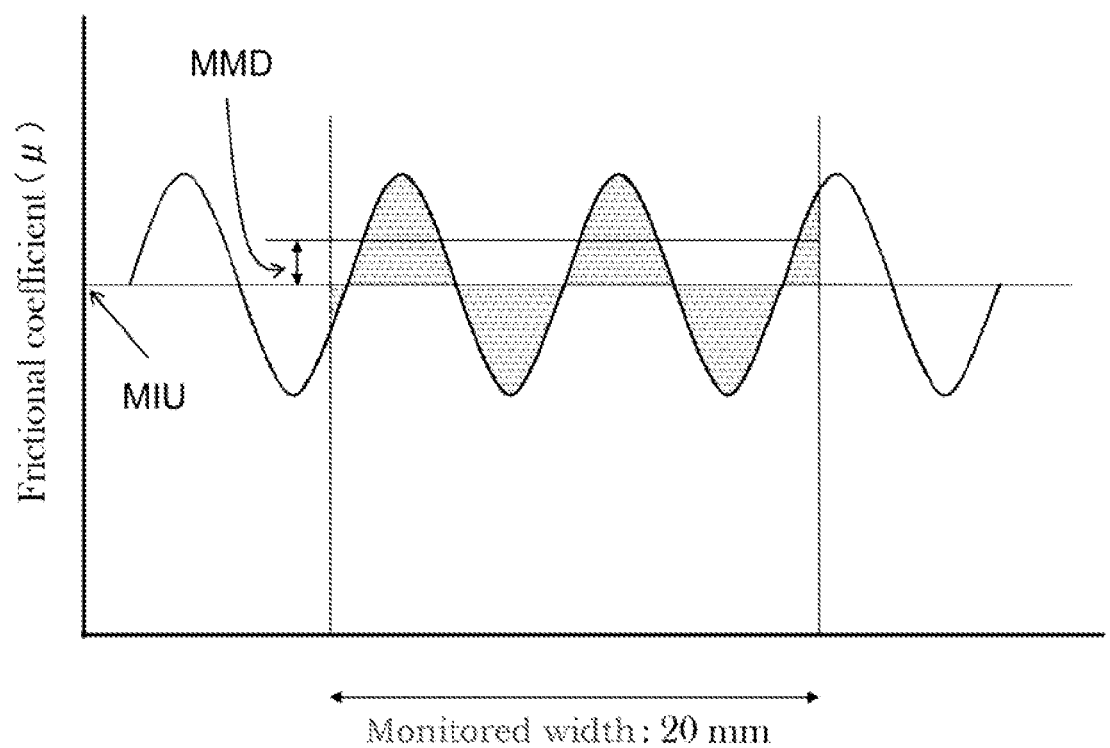
FIG. 3 shows a schematic illustration for determining the fluctuation of the average frictional coefficient (MMD) from a result of monitoring the frictional coefficient μ.

A schematic illustration for determining the fluctuation range of the average frictional coefficient (MMD) from a result of monitoring the frictional coefficient is shown in FIG. 3.

As shown in FIG. 3, in the monitored width of 20 mm, the integral of the absolute value of the difference between the average frictional coefficient (MIU) and the frictional coefficient μ is calculated (the shaded portion in FIG. 3). The fluctuation of the average frictional coefficient (MMD) is determined by dividing the integrated value by the monitored width (20 mm).

In case where the value of MMD is 0.005 to 0.010, it can be recognized that the smoothness of the surface is good.

Example 1

Into a storage tank A equipped with a stirrer and kept at 80° C., 100 parts by mass of thoroughly dried polyethylene oxide with a number average molecular weight of 20,000, 1.18 parts by mass of 1,6-hexanediol, 1.58 parts by mass of decyl alcohol and 0.1 part by mass of dioctyltin dilaurate were placed in such a proportion, and stirred under a nitrogen gas atmosphere to prepare a homogeneous mixture. Separately, into a storage tank B kept at 30° C., dicyclohexylmethane-4,4'-diisocyanate was placed and stored under a nitrogen gas atmosphere.

By using a quantitative pump, the mixture in the storage tank A and dicyclohexylmethane-4,4'-diisocyanate in the storage tank B were continuously supplied respectively at a rate of 200 [g/min] and 10.21 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

Example 2

Into a storage tank A equipped with a stirrer and kept at 80° C., 100 parts by mass of thoroughly dried polyethylene oxide with a number average molecular weight of 20,000, 1.18 parts by mass of 1,6-hexanediol, 1.29 parts by mass of octyl alcohol and 0.1 part by mass of dioctyltin dilaurate were placed in such a proportion, and stirred under a nitrogen gas atmosphere to prepare a homogeneous mixture. Separately, into a storage tank B kept at 30° C., dicyclohexylmethane-4,4'-diisocyanate was placed and stored under a nitrogen gas atmosphere.

By using a quantitative pump, the mixture in the storage tank A and dicyclohexylmethane-4,4'-diisocyanate in the storage tank B were continuously supplied respectively at a rate of 250 [g/min] and 12.78 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

Example 3

Into a storage tank A equipped with a stirrer and kept at 80° C., 100 parts by mass of thoroughly dried polyethylene oxide with a number average molecular weight of 10,000, 2.08 parts by mass of 1,9-nonanediol, 1.55 parts by mass of octyl alcohol and 0.1 part by mass of dioctyltin dilaurate were placed in such a proportion, and stirred under a nitrogen gas atmosphere to prepare a homogeneous mixture. Separately, into a storage tank B kept at 30° C., hexane diisocyanate was placed and stored under a nitrogen gas atmosphere.

By using a quantitative pump, the mixture in the storage tank A and hexane diisocyanate in the storage tank B were continuously supplied respectively at a rate of 167 [g/min] and 9.62 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

Example 4

Into a storage tank A equipped with a stirrer and kept at 80° C., 100 parts by mass of thoroughly dried ethylene oxide/propylene oxide (=75/25) with a number average molecular weight of 15,000, 1.04 parts by mass of 1,9-nonanediol, 1.29 parts by mass of octyl alcohol and 0.1 part by mass of dioctyltin dilaurate were placed in such a proportion, and stirred under a nitrogen gas atmosphere to prepare a homogeneous mixture. Separately, into a storage tank B kept at 30° C., hexane diisocyanate was placed and stored under a nitrogen gas atmosphere.

By using a quantitative pump, the mixture in the storage tank A and hexane diisocyanate in the storage tank B were continuously supplied respectively at a rate of 167 [g/min] and 5.60 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

Example 5

Into a storage tank A equipped with a stirrer and kept at 80° C., 100 parts by mass of thoroughly dried polyethylene oxide with a number average molecular weight of 6,000, 0.98 part by mass of 1,6-hexanediol, 2.53 parts by mass of hexyl alcohol and 0.1 part by mass of dioctyltin dilaurate were placed in such a proportion, and stirred under a nitrogen gas atmosphere to prepare a homogeneous mixture. Separately, into a storage tank B kept at 30° C., isophorone diisocyanate was placed and stored under a nitrogen gas atmosphere.

By using a quantitative pump, the mixture in the storage tank A and 3-isocyanatomethyl-3,5,5-trimethylcyclohexyl=isocyanate in the storage tank B were continuously supplied respectively at a rate of 200 [g/min] and 18.98 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

Comparative Example 1

Into a storage tank A equipped with a stirrer and kept at 80° C., 100 parts by mass of thoroughly dried polyethylene oxide with a number average molecular weight of 20,000, 1.57 parts by mass of decyl alcohol and 0.1 part by mass of dioctyltin dilaurate were placed in such a proportion, and stirred under a nitrogen gas atmosphere to prepare a homogeneous mixture. Separately, into a storage tank B kept at 30° C., dicyclohexylmethane-4,4'-diisocyanate was placed and stored under a nitrogen gas atmosphere.

By using a quantitative pump, the mixture in the storage tank A and dicyclohexylmethane-4,4'-diisocyanate in the storage tank B were continuously supplied respectively at a rate of 200 [g/min] and 4.54 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

Comparative Example 2

Into a storage tank A equipped with a stirrer and kept at 80° C., 100 parts by mass of thoroughly dried polyethylene oxide with a number average molecular weight of 20,000, 1.18 parts by mass of hexanediol, 0.04 part by mass of amyl alcohol and 0.1 part by mass of dioctyltin dilaurate were placed in such a proportion, and stirred under a nitrogen gas atmosphere to prepare a homogeneous mixture. Separately, into a storage tank B kept at 30° C., dicyclohexylmethane-4,4'-diisocyanate was placed and stored under a nitrogen gas atmosphere.

By using a quantitative pump, the mixture in the storage tank A and dicyclohexylmethane-4,4'-diisocyanate in the storage tank B were continuously supplied respectively at a rate of 250 [g/min] and 7.40 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

Comparative Example 3

Into a storage tank A equipped with a stirrer and kept at 80° C., 100 parts by mass of thoroughly dried polyethylene oxide with a number average molecular weight of 10,000, 2.08 parts by mass of 1,3-propanediol, 2.58 parts by mass of octyl alcohol and 0.1 part by mass of dioctyltin dilaurate were placed in such a proportion, and stirred under a nitrogen gas atmosphere to prepare a homogeneous mixture. Separately, into a storage tank B kept at 30° C., hexane diisocyanate was placed and stored under a nitrogen gas atmosphere.

By using a quantitative pump, the mixture in the storage tank A and hexane diisocyanate in the storage tank B were continuously supplied respectively at a rate of 167 [g/min] and 8.44 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a polyalkylene oxide-modified product.

The raw materials used and the evaluation results are shown in Table 1 and Table 2, respectively.

Comparative Example 4

Into a storage tank A equipped with a stirrer and kept at 80° C., 100 parts by mass of thoroughly dried ethylene oxide/propylene oxide (=75/25) with a number average molecular weight of 15,000, 2.08 parts by mass of propanediol, 2.02 parts by mass of octyl alcohol and 0.1 part by mass of dioctyltin dilaurate were placed in such a proportion, and stirred under a nitrogen gas atmosphere to prepare a homogeneous mixture. Separately, into a storage tank B kept at 30° C., hexane diisocyanate was placed and stored under a nitrogen gas atmosphere.

By using a quantitative pump, the mixture in the storage tank A and hexane diisocyanate in the storage tank B were continuously supplied respectively at a rate of 167 [g/min] and 11.77 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a polyalkylene oxide-modified product.

The raw materials used and the evaluation results are shown in Table 1 and Table 2, respectively.

Comparative Example 5

Into a storage tank A equipped with a stirrer and kept at 80° C., 100 parts by mass of thoroughly dried polyethylene oxide with a number average molecular weight of 20,000, 0.9 part by mass of trimethylol propane, 4.71 parts by mass of decyl alcohol and 0.1 part by mass of dioctyltin dilaurate were placed in such a proportion, and stirred under a nitrogen gas atmosphere to prepare a homogeneous mixture. Separately, into a storage tank B kept at 30° C., dicyclohexylmethane-4,4'-diisocyanate was placed and stored under a nitrogen gas atmosphere.

By using a quantitative pump, the mixture in the storage tank A and dicyclohexylmethane-4,4'-diisocyanate in the storage tank B were continuously supplied respectively at a rate of 167 [g/min] and 12.43 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the results are shown in Table 1 and Table 2, respectively.

Comparative Example 6

Into a storage tank A equipped with a stirrer and kept at 80° C., 100 parts by mass of thoroughly dried polyethylene oxide with a number average molecular weight of 20,000, 0.45 part by mass of trimethylol propane, 3.14 parts by mass of decyl alcohol and 0.1 part by mass of dioctyltin dilaurate were placed in such a proportion, and stirred under a nitrogen gas atmosphere to prepare a homogeneous mixture. Separately, into a storage tank B kept at 30° C., dicyclohexylmethane-4,4'-diisocyanate was placed and stored under a nitrogen gas atmosphere.

By using a quantitative pump, the mixture in the storage tank A and dicyclohexylmethane-4,4'-diisocyanate in the storage tank B were continuously supplied respectively at a rate of 167 [g/min] and 8.45 [g/min] into a biaxial extruder having screws with a 26-mm outer diameter (L/D=40), which was set to 110 to 140° C., were mixed in the extruder to perform a reaction. A strand was taken out of the outlet of the extruder and pelletized by means of a pelletizer to obtain a water-soluble polyalkylene oxide-modified product.

The raw materials used and the evaluation results are shown in Table 1 and Table 2, respectively.

TABLE 1

| | Polyalkylene oxide[1] | | | | | |
|---|---|---|---|---|---|---|
| | Type | Molecular weight | Diol[2] | Triol[3] | Hydrophobic alcohol | Diisocyanate[4] |
| Example 1 | Poly-EO | 20000 | HDO | — | Decyl alcohol | HMDI |
| Example 2 | Poly-EO | 20000 | HDO | — | Octyl alcohol | HMDI |
| Example 3 | Poly-EO | 10000 | NDO | — | Octyl alcohol | HDI |
| Example 4 | EO/PO | 15000 | NDO | — | Octyl alcohol | HDI |
| Example 5 | Poly-EO | 6000 | HDO | — | Hexyl alcohol | IPDI |
| Comparative Example 1 | Poly-EO | 20000 | — | — | Decyl alcohol | HMDI |
| Comparative Example 2 | Poly-EO | 20000 | HDO | — | Amyl alcohol | HMDI |
| Comparative Example 3 | Poly-EO | 10000 | PDO | — | Octyl alcohol | HDI |
| Comparative Example 4 | EO/PO | 15000 | PDO | — | Octyl alcohol | HDI |
| Comparative Example 5 | Poly-EO | 20000 | — | TMP | Decyl alcohol | HMDI |
| Comparative Example 6 | Poly-EO | 20000 | — | TMP | Decyl alcohol | HMDI |

[1]Poly-EO: polyethylene oxide, EO/PO: ethylene oxide/propylene oxide copolymer

[2]HDO: 1,6-hexanediol, NDO: 1,9-nonanediol, PDO: 1,3-propanediol

[3]TMP: trimethylol propane

[4]HMDI: dicyclohexylmethane-4,4'-diisocyanate, HDI: 1,6-hexamethylene diisocyanate IPDI: 3-isocyanatomethyl-3,5,5-trimethylcyclohexyl = isocyanate

TABLE 2

| | Concentration of urethane group [%] | Viscosity of 3% by mass aqueous solution [Pa · s] (water) | | | | | | Viscosity of 3% by mass aqueous solution [Pa · s] (3% by mass aqueous sodium chloride solution) | | | | | | Transmittance [%] 3% by mass | |
|---|---|---|---|---|---|---|---|---|---|---|---|---|---|---|---|
| | | 0.01 [1/s] | 0.1 [1/s] | 10 [1/s] | 100 [1/s] | Ti value A | Ti value B | 0.01 [1/s] | 0.1 [1/s] | 10 [1/s] | 100 [1/s] | Ti value A | Ti value B | Water | aqueous sodium chloride |
| Example 1 | 1.6 | 650 | 650 | 40 | 7.5 | 1.0 | 5.3 | 920 | 920 | 58 | 12.0 | 1.0 | 4.9 | 37 | 35 |
| Example 2 | 1.6 | 1020 | 1020 | 35 | 5.4 | 1.0 | 6.5 | 1540 | 1540 | 130 | 21 | 1.0 | 6.2 | 69 | 65 |
| Example 3 | 2.8 | 530 | 530 | 53 | 7.1 | 1.0 | 7.5 | 750 | 750 | 95 | 13 | 1.0 | 7.3 | 45 | 42 |
| Example 4 | 1.7 | 450 | 320 | 80 | 14.5 | 1.4 | 5.5 | 590 | 420 | 110 | 21 | 1.4 | 5.2 | 55 | 52 |
| Example 5 | 2.3 | 680 | 680 | 350 | 77.8 | 1.0 | 4.5 | 720 | 720 | 390 | 87 | 1.0 | 4.5 | 77 | 73 |
| Comparative Example 1 | 0.7 | 0.95 | 0.95 | 0.95 | 0.95 | 1.0 | 1.0 | 1.33 | 1.33 | 1.33 | 1.33 | 1.0 | 1.0 | 0.9 | 0.7 |
| Comparative Example 2 | 0.9 | 11.2 | 9.2 | 11.3 | 11.3 | 1.2 | 1.0 | 13.2 | 11.2 | 13.2 | 13.2 | 1.2 | 1.0 | 5.5 | 5.2 |
| Comparative Example 3 | 3.1 | Gelation | | | | — | — | Gelation | | | | — | — | — | — |
| Comparative Example 4 | 3.7 | Gelation | | | | — | — | Gelation | | | | — | — | — | — |
| Comparative Example 5 | 3.1 | Gelation | | | | — | — | Gelation | | | | — | — | — | — |
| Comparative Example 6 | 2.0 | 860 | 860 | 120 | 80 | 1.0 | 1.5 | 950 | 950 | 150 | 100 | 1.0 | 1.5 | 25 | 23 |

Ti value A = viscosity at a shear rate of 0.01 [1/s]/viscosity at a shear rate of 0.1 [1/s]
Ti value B = viscosity at a shear rate of 10 [1/s]/viscosity at a shear rate of 100 [1/s]

As shown in Table 2, the water-soluble polyalkylene oxide-modified product obtained by the present invention has high viscosity in an aqueous solution, good handling properties and coating properties, and is excellent in its transmittance.

(Preparation of Cold Cream)

Examples 6 to 10

With water-soluble polyalkylene oxide-modified products in Examples 1 to 5, cold creams as Examples 6 to 10 were obtained by the following formulation and preparation method.
The results are shown in Table 3.
(1) Formulation (Cold Cream)

| AQUPEC 501ER (manufactured by Sumitomo Seika Chemicals Company Limited) | 0.2 part by mass |
|---|---|
| A phase | |
| Octyl methoxycinnamate | 7.5 parts by mass |
| Octyl triazone | 1 part by mass |
| Liquid paraffin | 8 parts by mass |
| Tri(caprylic acid/capric acid)glyceryl | 1 part by mass |
| Cyclopentasiloxane | 2 parts by mass |
| Sorbitan monooleate | 0.1 parts by mass |
| Vitamin E acetate ester | 0.1 parts by mass |
| Phenoxyethanol | 1 part by mass |
| B phase | |
| Water-soluble polyalkylene oxide-modified product | 3.2 parts by mass |
| Propylene glycol | 5 parts by mass |
| Ceteareth-25 | 0.5 parts by mass |
| Water | 70.4 parts by mass |
| C phase | |
| Sodium hydroxide | 0.05 parts by mass |

(2) Preparation Method

To the previously thoroughly stirred A phase, 0.2 part by mass of AQUPEC 501ER was added and dispersed therein, after which phenoxyethanol was added. Then, the phase was slowly added to the B phase in which the contents had been completely dissolved, was subjected to homogenization (at 50° C. and 8000 rpm for 10 minutes) with a homogenizer, and was neutralized with sodium hydroxide to obtain a cold cream.

(Preparation of Shampoo)

Examples 11 to 15

With water-soluble polyalkylene oxide-modified products in Examples 1 to 5, shampoos as Examples 11 to 15 were obtained by the following formulation and preparation method.
The results are shown in Table 3.
(1) Formulation (Shampoo)

| A phase | |
|---|---|
| AQUPEC 501ER (manufactured by Sumitomo Seika Chemicals Company Limited) | 0.15 parts by mass |
| Water-soluble polyalkylene oxide-modified product | 0.15 parts by mass |
| Water | 14.7 parts by mass |
| B phase | |
| Ammonium dodecyl sulfate (25%) | 40.8 parts by mass |
| Ammonium laureth sulfate (23%) | 11.4 parts by mass |
| 5% Aqueous potassium hydroxide solution | 3.5 parts by mass |
| Water | 12.5 parts by mass |
| C phase | |
| Cocamide MEA | 1.5 parts by mass |
| Water | 12.4 parts by mass |
| Coconut oil fatty acid amide propyl dimethylamino acetic acid betaine (30%) | 2.4 parts by mass |
| Phenoxyethanol | 0.5 parts by mass |

(2) Preparation Method

In the A phase in which AQUPEC 501ER had been dispersed, a water-soluble polyalkylene oxide-modified product was dissolved and added with the B phase. To the mixture, the C phase was added and stirred for 15 minutes at 75° C. Finally, 2.4 parts by mass of coconut oil fatty acid amide propyl dimethylamino acetic acid betaine (30%) and 0.5 part by mass of phenoxyethanol were added to obtain a transparent shampoo.

Comparative Examples 7 to 9

With water-soluble polyalkylene oxide-modified products in Comparative Examples 1 to 3, by the preparation method described in Examples 6 to 10, cold creams as Comparative Examples 7 to 9, which have the same composition (except for the water-soluble polyalkylene oxide-modified product) as the cold creams in the examples, were obtained.

The results are shown in Table 3.

Comparative Examples 10 to 12

With water-soluble polyalkylene oxide-modified products in Comparative Examples 1 to 3, by the preparation method described in Examples 11 to 15, shampoos as Comparative Examples 10 to 12, which have the same composition (except for the water-soluble polyalkylene oxide-modified product) as the shampoos in the examples, were obtained.

The results are shown in Table 3.

TABLE 3

| | Polyalkylene oxide-modified product | Formulation | Viscosity [Pa · s] | MIU | MMD | Transmittance [%] |
|---|---|---|---|---|---|---|
| Example 6 | Example 1 | Cold cream | 198 | 0.38 | 0.008 | — |
| Example 7 | Example 2 | Cold cream | 155 | 0.33 | 0.009 | — |
| Example 8 | Example 3 | Cold cream | 220 | 0.28 | 0.007 | — |
| Example 9 | Example 4 | Cold cream | 188 | 0.31 | 0.008 | — |
| Example 10 | Example 5 | Cold cream | 125 | 0.26 | 0.006 | — |
| Comparative Example 7 | Comparative Example 1 | Cold cream | 65 | 0.58 | 0.015 | — |
| Comparative Example 8 | Comparative Example 2 | Cold cream | 96 | 0.53 | 0.017 | — |
| Comparative Example 9 | Comparative Example 6 | Cold cream | 160 | 0.45 | 0.018 | — |
| Example 11 | Example 1 | Shampoo | 120 | — | — | 83 |
| Example 12 | Example 2 | Shampoo | 135 | — | — | 90 |
| Example 13 | Example 3 | Shampoo | 155 | — | — | 85 |
| Example 14 | Example 4 | Shampoo | 160 | — | — | 88 |
| Example 15 | Example 5 | Shampoo | 185 | — | — | 95 |
| Comparative Example 10 | Comparative Example 1 | Shampoo | 35 | — | — | 32 |
| Comparative Example 11 | Comparative Example 2 | Shampoo | 48 | — | — | 35 |
| Comparative Example 12 | Comparative Example 6 | Shampoo | 48 | — | — | 49 |

As shown in Table 3, employing the water-soluble polyalkylene oxide-modified product obtained by the present invention makes it possible to obtain a cold cream which is good in slipperiness and has little stickiness and a shampoo having excellent transparency.

INDUSTRIAL APPLICABILITY

The present invention can provide a water-soluble polyalkylene oxide-modified product having a high thickening effect and excellent transparency. Moreover, it can provide a cosmetic material having little feeling of stickiness, a paint which is excellent in preventing the paint from dribbling and smoothness of the coating, and the like, which contain the water-soluble polyalkylene oxide-modified product.

The invention claimed is:

1. A water-soluble polyalkylene oxide-modified product obtained by reacting compounds consisting of a monovalent hydrophobic alcohol of the general formula (I):

[Chem. 1]

$$R^1\text{---}OH \quad (I)$$

wherein $R^1$ represents an alkyl group with 6 to 14 carbon atoms, a linear diol compound of the general formula (II):

[Chem. 2]

$$HO\text{---}R^2\text{---}OH \quad (II)$$

wherein $R^2$ represents a linear alkylene group with 5 to 10 carbon atoms, a polyalkylene oxide compound of the general formula (III):

[Chem. 3]

$$HO\text{---}(CH_2CHR^3\text{---}O)_n\text{---}H \quad (III)$$

wherein $R^3$ represents hydrogen atom or a methyl group and n represents an integer of 90 to 900, a diisocyanate compound of the general formula (IV):

[Chem. 4]

$$O\text{=}C\text{=}N\text{---}R^4\text{---}N\text{=}C\text{=}O \quad (IV)$$

wherein $R^4$ represents a methyl diphenylene group, a hexamethylene group, a methyl dicyclohexylene group, a 3-methyl-3,5,5-trimethyl cyclohexylene group, a dimethyl phenylene group or a tolylene group, and optionally a reaction accelerator, wherein the amount of the linear diol compound used is 0.5 to 2.5 moles relative to 1 mole of the polyalkylene oxide compound.

2. The water-soluble polyalkylene oxide-modified product according to claim 1, wherein the polyalkylene oxide compound is a polyalkylene oxide compound selected from the group consisting of polyethylene oxide with a number average molecular weight of 4,000 to 30,000 and a polyethylene oxide/polypropylene oxide copolymer with a number average molecular weight of 4,000 to 30,000.

3. The water-soluble polyalkylene oxide-modified product according to claim 1, wherein the amount of the hydrophobic alcohol used is 0.5 to 2.5 moles relative to 1 mole of the polyalkylene oxide compound.

4. The water-soluble polyalkylene oxide-modified product according to claim 1, wherein the diisocyanate compound is at least one selected from the group consisting of dicyclohexylmethane-4,4'-diisocyanate, 1,6-hexamethylene diisocyanate and 3-isocyanatomethyl-3,5,5-trimethylcyclohexyl-isocyanate.

5. An emulsion composition, comprising the water-soluble polyalkylene oxide-modified product according to claim 1 in an amount of 0.01 to 10% by mass.

6. A cosmetic material, comprising the water-soluble polyalkylene oxide-modified product according to claim 1 in an amount of 0.01 to 10% by mass.

7. The water-soluble polyalkylene oxide-modified product according to claim 1, wherein the reaction accelerator is selected from the group consisting of triethylamine, triethanolamine, dibutyltin diacetate, dibutyltin dilaurate, stannous octoate and triethylenediamine.

* * * * *